United States Patent [19]

Kobayashi et al.

[11] 4,434,179
[45] Feb. 28, 1984

[54] WOUND-HEALING PROMOTERS

[75] Inventors: Shinsaku Kobayashi; Akira Ogiso, both of Hiromachi, Japan

[73] Assignee: Sankyo Company, Limited, Tokyo, Japan

[21] Appl. No.: 353,887

[22] Filed: Mar. 2, 1982

[30] Foreign Application Priority Data

Mar. 17, 1981 [JP] Japan ................................ 56-38327

[51] Int. Cl.³ ................ A61K 31/235; A61K 31/075; A61K 31/045
[52] U.S. Cl. ................................ 424/308; 424/311; 424/312; 424/314; 424/339; 424/342; 424/343
[58] Field of Search ................ 424/343, 308, 312, 342

[56] References Cited

U.S. PATENT DOCUMENTS 4,059,641 11/1975 Mishima et al. ................ 260/635 R

FOREIGN PATENT DOCUMENTS 1533377 11/1978 United Kingdom .

*Primary Examiner*—Leonard Schenkman
*Attorney, Agent, or Firm*—Frishauf, Holtz, Goodman & Woodward

[57] ABSTRACT

Compounds of formula (I):

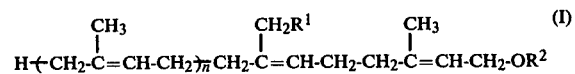

(wherein:
$R^1$ represents a hydroxy group, a $C_1$–$C_8$ alkoxy group, an aliphatic acyloxy group, a benzoyloxy group or a cinnamoyloxy group; pl $R^2$ represents a hydrogen atom, a $C_1$–$C_8$ alkyl group, an aliphatic acyl group, a benzoyl group or a cinnamoyl group; and
n represents an integer from 1 to 3)

when applied topically have been found to promote wound-healing and exuberant granulation; they are preferably formulated with a pharmaceutical topical base.

37 Claims, No Drawings

WOUND-HEALING PROMOTERS

BACKGROUND OF THE INVENTION

The present invention relates to the use of a known class of polyprenyl derivatives as wound-healing promoters and to a composition for topical application containing one or more of these polyprenyl derivatives as the active ingredient.

U.K. patent specification No. 1,533,377 and U.S. Pat. No. 4,059,641 disclose a class of polyprenyl derivatives which may be represented by the general formula:

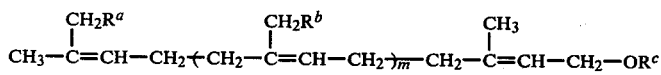

in which $R^a$ and $R^b$ are the same or different and each represents a hydrogen atom or a hydroxy, alkoxy or acyloxy group, $R^c$ represents a hydrogen atom or an alkyl or acyl group and m is an integer from 1 to 4. These compounds were found to be of value in the treatment of peptic ulcers and hence were administered orally or parenterally (e.g. by subcutaneous or intramuscular injection).

We have now discovered that certain of this known class of polyprenyl derivatives have a valuable and totally unexpected activity in that they assist granulation (which is part of the normal process of healing of a wound) and thus act to promote the healing of wounds. They are thus of value for topical application to wounds, as well as for the purposes previously disclosed.

BRIEF SUMMARY OF INVENTION

In one aspect, therefore, the present invention provides a method for the external treatment of wounds in humans and other animals, which method comprises applying topically to the site of the wound a compound having the formula (I):

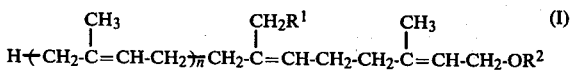

wherein:
  $R^1$ represents a hydroxy group, an alkoxy group having from 1 to 8 carbon atoms, an aliphatic acyloxy group, a benzoyloxy group or a cinnamoyloxy group;
  $R^2$ represents a hydrogen atom, an alkyl group having from 1 to 8 carbon atoms, an aliphatic acyl group, a benzoyl group or a cinnamoyl group; and
  n represents an integer from 1 to 3.

The invention also provides a composition for external use in humans and other animals, which comprises, as active ingredient, a compound of formula (I) incorporated in a topical pharmaceutical base.

DETAILED DESCRIPTION OF INVENTION

In the compounds of formula (I), when $R^1$ represents an alkoxy group, this may be a straight or branched chain alkoxy group and is preferably such a group having from 1 to 3 carbon atoms, for example a methoxy, ethoxy, propoxy or isopropoxy group. When $R^1$ represents an aliphatic acyloxy group, this is preferably such a group containing from 2 to 18 carbon atoms and may be a straight or branched chain group. Examples of such aliphatic acyloxy groups include alkanoyloxy groups, for example acetoxy, propionyloxy, butyryloxy, isobutyryloxy, valeryloxy, pivaloyloxy, caproyloxy, 2-methylvaleryloxy, heptanoyloxy, octanoyloxy, 2-ethylhexanoyloxy, nonanoyloxy, decanoyloxy, undecanoyloxy, lauroyloxy, myristyloxy, pentadecanoyloxy, palmitoyloxy and stearoyloxy groups, and alkenoyloxy groups, such as acryloyloxy, crotonyloxy, 3-butenoyloxy, methacryloyloxy, tigloyloxy, sorboyloxy, 10-undecenoyloxy and oleoyloxy groups.

When $R^2$ in the compounds of formula (I) represents an alkyl group, this may be a straight or branched chain group and preferably contains from 1 to 3 carbon atoms; examples of such groups include the methyl, ethyl, propyl and isopropyl groups. When $R^2$ represents an aliphatic acyl group, this preferably contains from 2 to 18 carbon atoms and examples include alkanoyl groups (such as acetyl, propionyl, butyryl, isobutyryl, valeryl, isovaleryl, pivaloyl, caproyl, 2-methylvaleryl, heptanoyl, octanoyl, 2-ethylhexanoyl, nonanoyl, decanoyl, undecanoyl, lauroyl, myristoyl, pentadecanoyl, palmitoyl and stearoyl groups) and alkenoyl groups (such as acryloyl, methacryloyl, tigloyl, sorboyl, 10-undecenoyl and oleoyl groups).

In general, it is preferred that, where $R^1$ represents a hydroxy group, $R^2$ should represent a hydrogen atom, where $R^1$ represents an alkoxy group, $R^2$ should represent an alkyl group which is the same as that of the alkoxy group and where $R^1$ represents an acyloxy group, $R^2$ should represent an acyl group which is the same as that of the acyloxy group, since such compounds are easiest to prepare; however, this is not an essential feature of the invention.

Particularly preferred compounds are those in which:
  $R^1$ represents a hydroxy group, a $C_2$–$C_{12}$ alkanoyloxy group, a $C_3$ or $C_4$ alkenoyloxy group, a cinnamoyloxy group, a benzoyloxy group or a $C_1$–$C_3$ alkoxy group;
  $R^2$ represents a hydrogen atom, a $C_2$–$C_{12}$ alkanoyl group, a $C_3$ or $C_4$ alkenoyl group, a cinnamoyl group, a benzoyl group or a $C_1$–$C_3$ alkyl group; and
  n is 1, 2 or 3, most preferably 2.

Because the various double bonds in the compounds of formula (I) can take various configurations, these compounds may exist as a number of geometric isomers and the present invention contemplates the use both of the individual isomers and of mixtures of 2 or more isomers. These configurations are designated in accordance with the E, Z designation recommended by the International Union of Pure and Applied Chemistry and described in the Journal of Organic Chemistry, 35, 2849 (1970).

Representative examples of compounds of formula (I) which may be used in the present invention include the following, all of which are disclosed in U.K. patent specification No. 1,533,377 and U.S. Pat. No. 4,059,641, and these compounds may be prepared as disclosed therein:

1. 7-Hydroxymethyl-3,11,15-trimethyl-2,6,10,14-hexadecatetraen-1-ol.
2. 1-Acetoxy-7-acetoxymethyl-3,11,15-trimethyl-2,6,10,14-hexadecatetraene.

3. 1-Crotonoyloxy-7-crotonoyloxymethyl-3,11,15-trimethyl-2,6,10,14-hexadecatetraene.
4. 1-Caproyloxy-7-caproyloxymethyl-3,11,15-trimethyl-2,6,10,14-hexadecatetraene.
5. 1-Cinnamoyloxy-7-cinnamoyloxymethyl-3,11,15-trimethyl-2,6,10,14-hexadecatetraene.
6. 1-Benzoyloxy-7-benzoyloxymethyl-3,11,15-trimethyl-2,6,10,14-hexadecatetraene.
7. 1-Lauroyloxy-7-lauroyloxymethyl-3,11,15-trimethyl-2,6,10,14-hexadecatetraene.
8. 1-Methoxy-7-methoxymethyl-3,11,15-trimethyl-2,6,10,14-hexadecatetraene.
9. 7-Hydroxymethyl-3,11-dimethyl-2,6,10-dodecatrien-1-ol.
10. 7-Hydroxymethyl-3,11,15,19-tetramethyl-2,6,10,14,18-eicosapentaen-1-ol.
11. 1-Acetoxy-7-acetoxymethyl-3,11,15,19-tetramethyl-2,6,10,14,18-eicosapentaene.
12. 1-Benzoyloxy-7-benzoyloxymethyl-3,11,15,19-tetramethyl-2,6,10,14,18-eicosapentaene.

The compounds listed above may exist as the following isomers:
Compounds 1-8: (E,Z,E), (E,E,E), (Z,E,E), (Z,Z,E), (Z,Z,Z), (Z,E,Z), (E,Z,Z,), and (E,E,Z) isomers;
Compound 9: (E,Z) and (E,E) isomers;
Compounds 10-12: (E,Z,E,E), (Z,E,E,E), (Z,Z,E,E), (E,Z,Z,E), (E,E,Z,E), (Z,Z,Z,E), (Z,E,Z,E), and (E,E,E,E) isomers.

These individual isomers may be separately prepared, as described in U.K. patent specification No. 1,533,377 and U.S. Pat. No. 4,059,641, or mixtures of the isomers may be prepared and the individual isomers then isolated by known methods. Alternatively, if desired, mixtures of isomers may be employed in the present invention.

The compounds of formula (I) very effectively promote the healing of wounds, as demonstrated in the following Experiments. In general, the major factors in the mechanism involved in wound-healing are exuberant granulation and subsequent proliferation of the connective tissues. Determination of the effect of the compounds of formula (I) on the progress of wound-healing was first demonstrated, in Experiment 1 by measuring the effect of the compounds on granulation.

Experiment 1

This test was conducted using the cotton pellet method described by Penn et al. [J. Pharm. Pharmacol., 15, 798 (1963)]. The test animals were male rats of the Wistar-Imamichi strain, each weighing about 250 g. The rats were employed in groups of five for each test. The cotton pellet used was formed from a cotton thread of length 8 mm, diameter 3 mm and weight 15±1 mg, defatted and dry-sterilized. The cotton pellet was impregnated with a solution of the test compound in 0.025 ml of ethanol and then dried, after which it was embedded subcutaneously in the back of the animal by means of a trocar, one pellet being inserted on each side of the animal. After 5 or 7 days, the granulation formed was excised and weighed first wet and then after drying at 70° C. to a constant weight.

The experiment was carried out in two runs, in each of which there was employed a control group where the cotton pellet was impregnated without any physiologically active substance. The test compounds used were Compound 1 [(E,Z,E)-7-hydroxymethyl-3,11,15-trimethyl-2,6,10,14-hexadecatetraen-1-ol] in various doses (Run 1) or cortisone alone or in admixture with Compound 1 (Run 2). The results are reported in Tables 1 and 2 and the weights given include that of the cotton thread (15 mg) and the results are reported as the mean of those achieved for the five animals in each group plus or minus the statistical error. Two results are reported for each experiment, the first being the wet weight and the second, in parenthesis, being the dry weight.

TABLE 1

(Run 1)

| Compound | Dose (mg) | After (days) | Wt (mg) of pellet | Statistical significance (cf control) |
|---|---|---|---|---|
| Control | — | 5 | 81.6 ± 6.6 | — |
|  |  |  | (27.7 ± 1.1) | — |
| Control | — | 7 | 60.5 ± 2.7 | — |
|  |  |  | (22.7 ± 0.9) | — |
| Cpd. 1 | 1 | 5 | 90.0 ± 7.1 | NS |
|  |  |  | (29.4 ± 2.1) | NS |
| Cpd. 1 | 1 | 7 | 86.2 ± 3.8 | P < 0.01 |
|  |  |  | (26.8 ± 0.8) | P < 0.05 |
| Cpd. 1 | 3 | 5 | 155.2 ± 13.4 | P < 0.01 |
|  |  |  | (37.3 ± 2.3) | P < 0.01 |
| Cpd. 1 | 3 | 7 | 114.2 ± 13.3 | P < 0.01 |
|  |  |  | (34.6 ± 2.4) | P < 0.01 |
| Cpd. 1 | 10 | 5 | 186.0 ± 16.4 | P < 0.01 |
|  |  |  | (44.7 ± 3.1) | P < 0.01 |
| Cpd. 1 | 10 | 7 | 217.0 ± 21.5 | P < 0.01 |
|  |  |  | (47.7 ± 3.3) | P < 0.01 |

NS: Not significant (P > 0.05)

TABLE 2

(Run 2)

| Compound (Dose, mg) | After (days) | Wt (mg) of pellet | Statistical significance cf control | cf cortisone alone |
|---|---|---|---|---|
| Control (—) | 5 | 102.2 ± 8.8 | — | — |
|  |  | (29.8 ± 1.5) | — | — |
| Control (—) | 7 | 67.1 ± 3.5 | — | — |
|  |  | (27.8 ± 1.3) | — | — |
| Cortisone (1) | 5 | 50.8 ± 1.8 | P < 0.01 | NS |
|  |  | (21.3 ± 0.4) | P < 0.01 | NS |
| Cortisone (1) | 7 | 52.7 ± 10.4 | NS | NS |
|  |  | (22.8 ± 1.6) | P < 0.05 | NS |
| Cortisone (1) + Cpd. 1 (3) | 5 | 77.9 ± 4.0 | P < 0.05 | NS |
|  |  | (25.9 ± 0.9) | P < 0.05 | P < 0.01 |
| Cortisone (1) + Cpd. 1 (3) | 7 | 98.5 ± 4.2 | P < 0.01 | P < 0.01 |
|  |  | (28.1 ± 0.9) | NS | P < 0.01 |

NS: Not significant (P > 0.05)

As can be seen from the above results, Compound 1 significantly increased the wet and dry weights of the granulation, thus demonstrating its ability to promote exuberant granulation. Furthermore, the same compounds significantly antagonised the inhibition of exuberant granulation which would otherwise have been caused by cortisone, which is known to have glucocorticoid activity, delaying wound-healing.

Experiment 2

The test animals used in this Experiment were male rats of the Wistar strain, each weighing about 300 g. The rats were employed in groups of six for each test.

Under pentobarbital anesthesia, the hair on the back was removed and the skin was incised along the median line to a length of about 6 cm. A piece of sponge 1×6×0.3 cm was then placed under the incision and the wound was sutured with clips at intervals of 1 cm. The clips were removed on the fourth day after the operation. The drug was applied by dropping a solution containing 2 mg/ml of Compound 1 in peanut oil onto the sponge in an amount of 0.5 ml immediately prior to the suture and in amounts of 0.67 ml immediately after and on the first and second days after the suture. The skin was peeled off on the 14th day after the suture and specimens of the skin were prepared with a width of 1 cm cut in a direction perpendicular to the incision line. The tension (g/cm) required to tear the skin was determined by drawing both ends at a constant rate.

One group of test animals were treated, as described above with Compound 1; another, control, group of animals was treated in the same way except that the peanut oil did not contain any drug. The results are shown in Table 3.

TABLE 3

|  | Control group | Treated group |
|---|---|---|
| Tensile | 765 | 859 |
| stress | 666 | 1112 |
| (g/cm) | 841 | 785 |
|  | 836 | 804 |
|  | 729 | 867 |
|  | 692 | 936 |
| Mean ± S.E. | 755 ± 30 | 894 ± 49 |
| Statistical significance |  | $P < 0.05$ |

As can be seen from the above Table, Compound 1 increases the tensile stress required for tearing at the wound site, thus indicating its ability to promote the healing of wounds.

The results of the above Experiments indicate that the compounds of the invention will be effective in the healing of wounds, including therapy of radiation-induced ulcers, decubitus ulcers, leg ulcers, trauma, chilblains, burns, general postoperative wounds and rectal wounds. For such uses, the compounds may be administered dissolved or dispersed in a pharmaceutical topical base. The pharmaceutical topical base may be of conventional type, as used in known pharmaceutical compositions intended for topical application, selected to suit the type of composition being formulated. The composition may similarly also contain one or more pharmaceutical adjuvents suited to that particular type of composition, such as emollients, humectants, dispersing agents, emulsifying agents, emulsion stabilisers, gelling agents, suspending agents, preservatives, percutaneous absorption promoters and aerosol propellants. The composition may typically contain such ingredients as natural or synthetic oils, waxes, fats, paraffins, petrolatum, higher fatty alcohols, wool alcohols, higher fatty acids, glycerides, soaps, sorbitan esters, polysorbates, macrogol esters and cellulose ethers.

Thus, for examples, compositions in accordance with the invention may be formulated as ointments, topical creams, lotions, emulsions, pastes, plasters, aqueous and non-aqueous liquids and aerosols, especially ointments, topical creams, lotions and pastes. Alternatively, it may be formulated as a suppository. In each case, the formulation, whether applied as an ointment or the like or as a suppository, preferably contains from 1 to 5% by weight of the active ingredient and may be applied one or more times each day. Examples of ingredients for the various formulations are as follows:

Ingredients for oily ointments

Oils and waxes: olive oil, almond oil, castor oil, sesame oil, cottonseed oil, palm oil, arachis oil, peanut oil, lanolin, ceresin, beeswax, carnauba wax, spermaceti, microcrystalline wax, paraffin (solid and liquid), squalane, squalene, petrolatum.

Fatty acids: stearic acid, palmitic acid, myristic acid.

Alcohols: stearyl alcohol, cetyl alcohol, oleyl alcohol.

Others: "Plastibase" (polyethylene dispersed in liquid paraffin).

| Ingredients for emulsions | |
|---|---|
| (a) Water-in-oil emulsions | |
| 1. Petrolatum | 90% |
| Sorbitan sesquioleate | 10% |
| 2. Beeswax | 5% |
| Petrolatum | 60% |
| Mineral oil | 25% |
| Sorbitan sesquioleate | 10% |
| 3. Petrolatum | 54% |
| Sorbitan sesquioleate | 6% |
| Water | 40% |
| Preservatives | q.s |
| 4. Petrolatum | 40% |
| Mineral oil | 15% |
| Beeswax | 4% |
| Sorbitan sesquioleate | 6% |
| Water | 35% |
| Preservatives | q.s. |
| 5. Mineral oil | 50% |
| Beeswax | 10% |
| Lanolin | 3.1% |
| Sorbitan sesquioleate | 1.0% |
| Borax | 0.7% |
| Water | 35.2% |
| Preservatives | q.s. |
| (b) Oil-in-water emulsions | |
| 1. Mineral oil | 20% |
| Cetyl alcohol | 2% |
| Petrolatum | 5% |
| Glyceryl monostearate | 3% |
| Polysorbate 60 | 7% |
| Water | 63% |
| Preservatives | q.s. |
| 2. Stearyl alcohol | 25% |
| Petrolatum | 25% |
| Propylene glycol | 12% |
| Polyoxyethylene stearate | 5% |
| Methyl paraben | 0.2% |
| Propyl paraben | 0.2% |
| Water | 33% |
| 3. Stearic acid | 20% |
| Isopropyl myristate | 1% |
| Glyceryl monostearate | 2% |
| Polysorbate 60 | 8% |
| Sorbitol solution | 20% |
| Water | 49% |
| Preservatives | q.s. |
| 4. Stearic acid | 1.5% |
| Glyceryl monostearate | 8% |
| Cetyl alcohol | 5% |
| Stearyl alcohol | 5% |
| Isopropyl myristate | 4% |
| Triethanolamine | 0.5% |
| Methyl paraben | 0.1% |
| Propyl paraben | 0.2% |
| Water | ad. 100% |
| 5. Cetostearyl alcohol | 3.5% |
| Isopropyl myristate | 6% |
| Sodium lauryl sulfate | 1% |
| Methyl paraben | 0.1% |
| Propyl paraben | 0.2% |
| Glycerol | 8% |
| Water | ad. 100% |
| (c) Oil-in-water lotion | |
| Mineral oil | 20% |
| Cetyl alcohol | 2% |
| Petrolatum | 5% |
| Glyceryl monostearate | 3% |
| Polysorbate 60 | 7% |
| Water | 63% |
| Preservatives | q.s. |
| Ingredients for water-soluble preparations | |
| (a) Macrogol base | |
| Macrogol 4,000 | 55% |
| Macrogol 400 | 35% |
| Glycerol | 10% |

-continued (b) Gel bases

| | | |
|---|---|---|
| 1. | "Carbopol 940" (carboxyvinyl polymer) | 1.0% |
| | Hydroxyethylcellulose | 1.0% |
| | Macrogol 300 | 10% |
| | Ethanol | 30% |
| | Diisopropyl adipate | 20% |
| | Diisopropanolamine | 1.1% |
| | Water | ad. 100% |
| 2. | "Carbopol 940" (carboxyvinyl polymer) | 0.4% |
| | Ethylene oxide oleyl alcohol ether | 2.5% |
| | "Polyox" resin WSR N-3000 (methylcellulose and ethylene oxide copolymer) | 0.2% |
| | "Ucon 50H B660" fluid | 10% |
| | PVP | 1.5% |
| | Glycerol | 5% |
| | Diisopropanolamine (10%) | 3% |
| | Water | ad. 100% |

The above compositions may also contain percutaneous absorption promoters, such as dimethyl sulfoxide, propyl gallate, diisopropyl adipate, diethyl sebacate and ethyl caproate.

Examples of formulations are given below, in which the active principle is (E,Z,E)-7-hydroxymethyl-3,11,15-trimethyl-2,6,10,14-hexadecatetraen-1-ol.

EXAMPLE 1

Ointment

This was prepared by conventional means using the following formulation:
Active principal: 1.0 g
Olive oil: 20 g
White vaseline: to 100 g in total

EXAMPLE 2

Topical cream

The following mixture was prepared:
Active principal: 1.0 g
Olive oil: 5.0 g
Cetanol: 2.0 g
Stearic acid: 5.0 g
Glycerin aliphatic acid ester: 12.0 g
Tween 60: 5.0 g
Meanwhile, the following mixture was also prepared:
Propylene glycol: 5.0 g
Methyl paraben: 0.1 g
Propyl paraben: 0.02 g
Purified water: to 100 g in total
These two were then blended together by conventional means to give a total of 100 g of a 100% by weight topical cream.

EXAMPLE 3

Suppository 3 g of active principal were blended with 97 g of Witepsol (trade name) W-35 to prepare a 3% suppository.

We claim:

1. A method for the external treatment of wounds in humans and other animals, which method comprises applying topically to the site of the wound a compound having the formula (I):

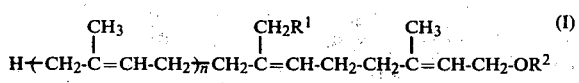

wherein:
R$^1$ represents a hydroxy group, a C$_1$–C$_8$ alkoxy group, a straight or branched C$_2$–C$_{18}$ aliphatic acyloxy group, a benzoyloxy group or a cinnamoyloxy group;
R$^2$ represents a hydrogen atom, a C$_1$–C$_8$ alkyl group, a C$_2$–C$_8$ aliphatic acyl group, a benzoyl group or a cinnamoyl group; and
n represents an integer from 1 to 3
in an amount effective to promote healing of the wound.

2. The method as claimed in claim 1, wherein, in said compound of formula (I) wherein:
R$^1$ represents a hydroxy group, a C$_1$–C$_3$ alkoxy group, a C$_2$–C$_{18}$ alkanoyloxy or a C$_2$–C$_{18}$ alkenoyloxy group, a benzoyloxy group or a cinnamoyloxy group;
R$^2$ represents a hydrogen atom, a C$_1$–C$_3$ alkyl group, a C$_2$–C$_{18}$ alkanoyl or a C$_2$–C$_{18}$ alkenoyl group, a benzoyl group or a cinnamoyl group; and
n represents an integer from 1 to 3.

3. The method as claimed in claim 1, wherein R$^1$ represents a group of formula —OR$^2$ and the two atoms or groups represented by R$^2$ in said compound of formula (I) are the same.

4. The method as claimed in claim 1, wherein said compound is 7-hydroxymethyl-3,11,15-trimethyl-2,6,10,14-hexadecatetraen-1-ol.

5. The method as claimed in claim 4, wherein said compound is the (E,Z,E) isomer.

6. A pharmaceutical composition for external use comprising between 1 and 5% by weight of the composition, of a compound of formula (I):

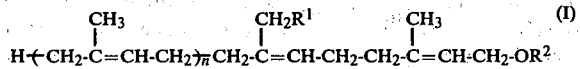

wherein:
R$^1$ represents a hydroxy group, a C$_1$–C$_8$ alkoxy group, a straight or branched C$_2$–C$_{18}$ aliphatic acyloxy group, a benzoyloxy group or a cinnamoyloxy group;
R$^2$ represents a hydrogen atom, a C$_1$–C$_8$ alkyl group, a C$_2$–C$_{18}$ aliphatic acyl group, a benzoyl group or a cinnamoyl group; and
n represents an integer from 1 to 3;
dissolved or dispersed in a pharmaceutical topical base selected from the group consisting of a topical ointment, a topical lotion suppository, and a topical paste.

7. The composition as claimed in claim 6, wherein, in said compound of formula (I) wherein:
R$^1$ represents a hydroxy group, a C$_1$–C$_3$ alkoxy group, a C$_2$–C$_{18}$ alkanoyloxy or a C$_2$–C$_{18}$ alkenoyloxy group, a benzoyloxy group or a cinnamoyloxy group;
R$^2$ represents a hydrogen atom, a C$_1$–C$_3$ alkyl group, a C$_2$–C$_{18}$ alkanoyl or a C$_2$–C$_{18}$ alkenoyl group, a benzoyl group or a cinnamoyl group; and
n represents an integer from 1 to 3.

8. The composition as claimed in claim 6, wherein R$^1$ represents a group of formula —OR$^2$ and the two atoms or groups represented by R$^2$ in said compound of formula (I) are the same.

9. The composition as claimed in claim 6, wherein said compound is 7-hydroxymethyl-3,11,15-trimethyl-2,6,10,14-hexadecatetraen-1-ol.

10. The composition as claimed in claim 9, wherein said compound is the (E,Z,E) isomer.

11. The composition as claimed in claim 6, wherein said topical base is a topical cream.

12. The composition as claimed in claim 6, wherein said topical base is a suppository.

13. The composition as claimed in claim 7, wherein said topical base is a topical paste.

14. The composition as claimed in claim 6, wherein said aliphatic acyloxy groups are selected from the group consisting of acetoxy, propionyloxy, butyryloxy, isobutyryloxy, valeryloxy, pivaloyloxy, caproyloxy, 2-methylvaleryloxy, heptanoyloxy, octanoyloxy, 2-ethylhexanoyloxy, nonanoyloxy, decanoyloxy, undecanoyloxy, lauroyloxy, myristyloxy, pentadecanoyloxy, palmitoyloxy, stearoyloxy, acryloyloxy, crotonyloxy, 3-butenoyloxy, methacryloyloxy, tigloyloxy, sorboyloxy, 10-undecenoyloxy and oleoyloxy groups.

15. The composition as claimed in claim 6, wherein said compound is 1-acetoxy-7-acetoxymethyl-3,11,15-trimethyl-2,6,10,14-hexadecatetraene.

16. The composition as claimed in claim 6, wherein said compound is 1-crotonoyloxy-7-crotonoyloxymethyl-3,11,15-trimethyl-2,6,10,14-hexadecatetraene.

17. The composition as claimed in claim 6, wherein said compound is 1-caproyloxy-7-caproyloxymethyl-3,11,15-trimethyl-2,6,10,14-hexadecatetraene.

18. The composition as claimed in claim 6, wherein said compound is 1-cinnamoyloxy-7-cinnamoyloxymethyl-3,11,15-trimethyl-2,6,10,14-hexadecatetraene.

19. The composition as claimed in claim 6, wherein said compound is 1-benzoyloxy-7-benzoyloxymethyll-3,11,15-trimethyl-2,6,10,14-hexadecatetraene.

20. The composition as claimed in claim 6, wherein said compound is 1-lauroyloxy-7-lauroyloxymethyl-3,11,15-trimethyl-2,6,10,14-hexadecatetraene.

21. The composition as claimed in claim 6, wherein said compound is 1-methoxy-7-methoxymethyl-3,11,15-trimethyl-2,6,10,14-hexadecatetraene.

22. The composition as claimed in claim 6, wherein said compound is 7-hydroxymethyl-3,11-dimethyl-2,6,10-dodecatrien-1-ol.

23. The composition as claimed in claim 6, wherein said compound is 7-hydroxymethyl-3,11,15,19-tetramethyl-2,6,10,14,18-eicosapentaene-1-ol.

24. The composition as claimed in clam 6, wherein said compound is 1-acetoxy-7-acetoxymethyl-3,11,15,19-tetramethyl-2,6,10,14,18-eicosapentaene.

25. The composition as claimed in claim 6, wherein said compound is 1-benzoyloxy-7-benzoyloxymethyl-3,11,15,19-tetramethyl-2,6,10,14,18-eicosapentaene.

26. The method as claimed in claim 1, wherein said aliphatic acyloxy groups are selected from the group consisting of acetoxy, propionyloxy, butyryloxy, isobutyryloxy, valeryloxy, pivaloyloxy, caproyloxy, 2-methylvaleryloxy, heptanoyloxy, octanyloxy, 2-ethylhexanoyloxy, nonanoyloxy, decanoyloxy, undecanoyloxy, lauroyloxy, myristyloxy, pentadecanoyloxy, palmitoyloxy, stearoyloxy, acryloyloxy, crotonyloxy, 3-butenoyloxy, methacryloyloxy, tigloyloxy, sorboyloxy, 10-undecenoyloxy and oleoyloxy groups.

27. The method as claimed in claim 1, wherein said compound is 1-acetoxy-7-acetoxymethyl-3,11,15-trimethyl-2,6,10,14-hexadecatetraene.

28. The method as claimed in claim 1, wherein said compound is 1-crotonoyloxy-7-crotonoyloxymethyl-3,11,15-trimethyl-2,6,10,14-hexadecatetraene.

29. The method as claimed in claim 1, wherein said compound is 1-caproyloxy-7-caproyloxymethyl-3,11,15-trimethyl-2,6,10,14-hexadecatetraene.

30. The method as claimed in claim 1, wherein said compound is 1-cinnamoyloxy-7-cinnamoyloxymethyl-3,11,15-trimethyl-2,6,10,14-hexadecatetraene.

31. The method as claimed in claim 1, wherein said compound is 1-benzoyloxy-7-benzoyloxymethyl-3,11,15-trimethyl-2,6,10,14-hexadecatetraene.

32. The method as claimed in claim 1, wherein said compound is 1-lauroyloxy-7-lauroyloxymethyl-3,11,15-trimethyl-2,6,10,14-hexadecatetraene.

33. The method as claimed in claim 1, wherein said compound is 1-methoxy-7-methoxymethyl-3,11,15-trimethyl-2,6,10,14-hexadecatetraene.

34. The method as claimed in claim 1, wherein said compound is 7-hydroxymethyl-3,11-dimethyl-2,6,10-dodecatrien-1-ol.

35. The method as claimed in claim 1, wherein said compound is 7-hydroxymethyl-3,11,15,19-tetramethyl-2,6,10,14,18-eicosapentaene-1-ol.

36. The method as claimed in claim 1, wherein said compound is 1-acetoxy-7-acetoxymethyl-3,11,15,19-tetramethyl-2,6,10,14,18-eicosapentaene.

37. The method as claimed in claim 1, wherein said compound is 1-benzoyloxy-7-benzoyloxymethyl-3,11,15,19-tetramethyl-2,6,10,14,18-eicosapentaene.

* * * * *